(12) United States Patent
Chen

(10) Patent No.: US 7,794,703 B1
(45) Date of Patent: Sep. 14, 2010

(54) METHOD FOR PRODUCTION AND DELIVERY OF A PROTEIN IN VIVO

(76) Inventor: Hai Xing Chen, 875 Glencairn Avenue, Toronto, Ontario (CA) M6B 2A4

( * ) Notice: Subject to any disclaimer, the term of this patent is extended or adjusted under 35 U.S.C. 154(b) by 0 days.

(21) Appl. No.: 12/634,011

(22) Filed: Dec. 9, 2009

Related U.S. Application Data

(63) Continuation of application No. 12/157,084, filed on Jun. 6, 2008, now abandoned, which is a continuation of application No. 10/917,208, filed on Aug. 12, 2004, now abandoned, which is a continuation of application No. 09/253,573, filed on Feb. 19, 1999, now abandoned.

(51) Int. Cl.
*A61K 48/00* (2006.01)
*A61K 31/70* (2006.01)
*A01N 63/00* (2006.01)
*C07H 21/04* (2006.01)
*C12N 15/86* (2006.01)

(52) U.S. Cl. .................. 424/93.21; 424/93.3; 424/577; 536/23.2; 536/23.5; 536/23.52; 536/23.53; 514/44; 435/456; 435/372

(58) Field of Classification Search ....................... None
See application file for complete search history.

(56) References Cited

U.S. PATENT DOCUMENTS 5,252,479 A * 10/1993 Srivastava ................ 435/235.1

OTHER PUBLICATIONS

Frey et al (Blood 91(8): 2781-2792, 1998).*
Hayakawa et al (Hum. Gene Ther. 20(6): 563-572, 2009).*

* cited by examiner

*Primary Examiner*—Richard Schnizer
(74) *Attorney, Agent, or Firm*—Yi Li

(57) ABSTRACT

A method for production and delivery of a protein in vivo is described. The method includes steps of inserting a promoter and a gene encoding a protein in a vector, collecting an amount of host cells from a mammal, treating the host cells in vitro with the vector, then introducing the treated cells back to the mammal. In vivo, the treated host cells produce red blood cells and the protein which is contained in the red blood cells. The protein is released into peripheral blood of the mammal through a natural or an induced rupture of the red blood cells to supply the protein to the body.

4 Claims, 2 Drawing Sheets

METHOD FOR PRODUCTION AND DELIVERY OF A PROTEIN IN VIVO

CROSS REFERENCE TO RELATED APPLICATION

This application is a continuation of patent application Ser. No. 12/157,084, filed Jun. 6, 2008, which is a continuation of patent application Ser. No. 10/917,208, filed Aug. 12, 2004, now abandoned, which is a continuation of patent application Ser. No. 09/253,573, filed Feb. 19, 1999, now abandoned. All parent applications are hereby incorporated by reference in their entirety.

FIELD OF THE INVENTION

The present invention relates to a method for production and delivery of a protein in vivo. In particular it relates to the method of producing a protein in the precursors of the red blood cells and utilizing the red blood cells to deliver the protein into the blood stream.

BACKGROUND OF THE INVENTION

After significant progress in the technology of gene therapy, the concept of using gene therapy to cure or alleviate inherited and acquired diseases has been accepted. Investigators have accomplished the requisite first steps: it has been shown that transferred genes can be induced to function in the human body. So far, however, no approach has definitively improved the health of one of the more than 2,000 patients who have enrolled in gene therapy trials worldwide. This lack of a convincing therapeutic benefit may reflect researchers' imperfect initial groping toward a difficult new technology and that the obstacles are more formidable than expected.

An individual gene in the human cell is a stretch of DNA that, in most cases, acts as a blueprint for making a specific protein. All cells in a body carry the same genes in the chromosomes of the nucleus. But different cells use, or express distinct subsets of genes and hence make separate sets of proteins.

The regulation of the difference in gene expression, according to the cell type (and cell needs), is controlled by different DNA fragment named promoter and/or enhancer in different cells. Only with the promoter, and sometimes together with enhancer, will genes be expressed. The gene expression is a two step process. The first is transcription that generates RNA from DNA template, and the second is translation that synthesizes protein from RNA template.

After completion of the protein synthesis, the proteins will be transported from their manufacture sites to their destined functional sites. There are two pathways for proteins to export from the cells where they are synthesized. The first pathway is constitutive secretion. This pathway presents a mechanism for bulk flow of proteins and lipids. The second pathway is a regulated process named exocytosis. In this pathway, a protein will only be released upon receiving a specific triggering signal, for instance, triggered by a hormone.

The mechanisms of natural protein synthesis and exportation are the main reasons that the primary research effort in gene therapy in the past decades and present has been focused on tissue or cell specific approaches. Researchers have been searching for tissue specific genes and methods to deliver them into their target organs or tissue, where the proteins are synthesized naturally, and the native proteins are exported and delivered to their functional sites through native pathways. For instance, naturally haemophilia factor XIII and human serum albumin are produced in liver cells and then exported into blood stream for their functions. Insulin is produced in pancreas beta-cells and also exported into blood stream for its function.

Although specific delivery of therapeutic genes into their native manufacturing sites is the ideal scheme for gene therapy, it is difficult to practice either in vivo or in vitro. In vitro, it is almost impossible to harvest enough target cells to introduce therapeutic genes into them. In turn, harvested target cells are not able to synthesize sufficient amount of proteins for the purpose of therapy. In vivo, a therapeutic gene has an equivalent probability entering any type of cells, regardless whether they are in the form of retroviral vector, liposome harbored retroviral vector or naked DNA. Consequently few of the DNA (therapeutic gene) will be delivered into its target cells. Therefore, the success of the current gene therapy approach critically depends on whether a tissue specific gene can be delivered specifically to the target organ or tissue. Despite tremendous effort and investment, the tissue specific approach has been found extremely difficult and unsuccessful so far.

On the other hand, non-tissue specific approaches also encounter serious obstacles. Although many cell types in the body are easy to obtain, such as muscle or skin cells, there are disadvantages with using non-tissue specific cells as host cells for gene therapy. In some cases, the host cells naturally do not posses the above described two protein export mechanisms. In other cases, even if the host cells do posses these export mechanisms for their native proteins, they do not function equivalently in the export of a non-native or guest protein. Low efficiency in exporting guest protein or complete blockage of the native export pathway has been reported.

Recently, gene therapy has achieved major progress by utilizing the native ability of viruses to enter cells, bringing their own genetic material with them. Many of these organisms have now been engineered to serve as vectors, or delivery vehicles, for gene transfer. Among variety of viruses, retroviruses are the most promising gene-delivery systems studied so far (Friedmann, Scientific American, June 1997, 96). Retroviruses convert their RNA to DNA in infected cells and insinuate the DNA into a chromosome. The integrated DNA then directs the synthesis of viral proteins.

Under normal circumstances, integrated retroviral DNA would direct the synthesis of viral proteins and RNA, which would then assemble into clones of the original virus. A method has been developed to alter retrovirus. The altered retrovirus, bereft of instructions for making viral proteins, produces no progeny. The virus essentially disappears from the cell, leaving behind only the foreign gene and nucleotide sequences that now serve merely to facilitate the expression of the gene.

U.S. Pat. No. 5,399,346 (to Anderson et al.) discloses a process for providing a human with a therapeutic protein. The process comprises inserting a DNA segment encoding a therapeutic protein into primary human cells, and introducing the primary human cells into a human. The primary human cells express and secret therapeutic protein in vivo. Anderson et al. further disclose that the primary human cells are nucleated blood cells, as well as progenitor and precursors thereof, which are capable of expanded growth in culture. Moreover, Anderson et al. teach that the genetically engineered cells can be combined with a pharmaceutically acceptable carrier for suitable administration to the human body. The carrier may be a liquid (e.g., a saline solution) or a solid carrier, e.g., an implant. In employing a liquid carrier, the engineered cells may be introduced, e.g., intravenously, sub-cutaneously, intramuscularly, intraperitoneally, intralesionaly, etc. Anderson et al. teach that the function of the therapeutic protein resides in the natural or modified function of the primary human cells in vivo.

One of the earliest gene therapies for curing human diseases was to use genetic engineered hemoglobin for treating beta thalassemia, a disorder of hemoglobin. Red blood cells of patients having beta thalassemia are deficient in beta globin, which in healthy individuals combines with alpha globin and heme to yield hemoglobin. The lack of beta globin gives rise a deficit in hemoglobin production and an excess of alpha globin, which in turn cause severe anemia. Researchers used beta globin promoter and beta globin gene (native to the red blood cells) to produce the desired beta globin. In these types of applications, the hemoglobin promoter has not been utilized in genetic engineering of heterologous proteins (non-native to the red blood cells) in red blood cells.

On the other hand, variety of native promoters have been used in constructing vectors carrying genes encoding therapeutic proteins that are either native or heterologous to the host cells. However, because of the concentrated effort in tissue specific gene therapy approach, the constructed vectors are essentially focused on the nucleated cells which have surface markers for specific target delivery of the cells.

Recently, various nonviral methods for therapeutic gene transfer have also been developed. For instance, liposomes have been used to harbor a retroviral vector (a stable loop of DNA derived from bacterial viruses known as phages) in which original genes have been replaced by those intended to be therapeutic. Injection of naked DNA (without lipid wrapping) into patients has also been explored. The naked DNA, injected into the muscle of an animal, was expressed as protein and a quite high local concentration of protein was obtained (Feigner, Scientific American, June 1997, 102). However, the local high concentration of protein produced inside the muscle would not have been sufficient to be effective against diseases like diabetes or hemophilias when the proteins are diluted into the three liters of plasma contained in the blood stream.

It is apparent that there is a strong need for new strategies and methods to overcome difficulties in gene therapy and to achieve the goal of synthesis and delivery of a sufficient amount of proteins in vivo.

SUMMARY OF THE INVENTION

A method for producing and delivering protein in vivo is provided. In one embodiment, the method comprises the steps of (1) insert a promoter and a gene encoding a protein in a vector, (2) collect an amount of host cells from a mammal, (3) treat the host cells in vitro with the vector, (4) introduce the treated host cells back to the mammal. The treated host cells produce red blood cells and the protein in vivo, wherein the protein is contained only in the red blood cells. Thereafter, the protein is released into blood stream of the mammal through rupture of the red blood cells. Optionally, the method also comprises inserting one or more enhancers in the vector.

In another embodiment, the method comprises steps of: (1) insert a hemoglobin promoter and a gene encoding a non-hemoglobin protein in a vector; (2) collect an amount of mammalian host cells from a mammal; (3) treat the host cells in vitro with the vector described above, (4) introduce the treated host cells back to the mammal. After reintroduction of the treated host cells back into the mammal, the host cells produce blood cells in vivo. The protein is contained only in the red blood cells because the inserted hemoglobin promoter in the vector is only active in the precursors of the red blood cells. The red blood cells rupture at the end of their life cycle and release the protein into blood stream.

With the method of the present invention, the vector is a viral vector and it is depleted of the segments responsible for viral expression. Preferably, the vector is a retroviral vector, a lentiviral vector, and an adenoviral vector.

The promoter suitable for the method of the present invention is a natural promoter of a gene, which enables initiation of a gene to express a protein in the progenitor cells of the red blood cells. Alternatively, the promoter may also be a mutated promoter of a gene. Preferably, the promoter is a hemoglobin promoter.

The host cells suitable for the method of the present invention are stem cells, and other progenitor cells of red blood cells.

The method of the present invention not only utilizes the stem cells and progenitor cells of red blood cells as the manufacture site for the production of proteins, but also uses the red blood cells as the delivery vehicle of the proteins. The proteins are released into blood stream through rupture of the red blood cells.

The rupture of the red blood cells can be a natural or an induced process. With the method of the present invention, because of the continuous production of the red blood cells and the proteins in vivo, a continuous protein supply will be provided to the patient for the purpose of therapy.

The proteins that may be synthesized and delivered by the method of the present invention include, but not limited to, antibody, enzyme, cofactor, interferon, hormone, and peptide. Furthermore, the proteins include natural proteins, fusion proteins, and mutated proteins.

One object of the present invention is to provide a non-tissue specific method that utilizes suitable host cells for synthesis of proteins.

Another object of the present invention is to specifically control the expression and production of proteins in the precursors of the red blood cells.

A further object of the present invention is to utilize vast production of natural red blood cells to provide an efficient protein synthesis and a sufficient supply of protein for the purpose of therapy. An additional object is to utilize the non nucleated cell nature of the red blood cells to provide an environment that benefits the stability of the proteins after their production.

Yet another object of the present invention is to bypass the secretion and exocytosis pathways for protein release from the manufacturing site; instead, to utilize the rupture of the red blood cells at the end of their life cycle as a delivery mechanism to provide an efficient delivery of the protein into blood stream.

Another object of the present invention is to use hemoglobin promoter to achieve the control of the expression and synthesis of proteins in the precursors of the red blood cells. In addition, use the strength of hemoglobin promoter to promote efficiency of the protein synthesis.

A further object of the present invention is to produce a broad spectrum of protein using a common mechanism for treatment of various health conditions.

DETAILED DESCRIPTION OF PREFERRED EMBODIMENTS

Figure 1:
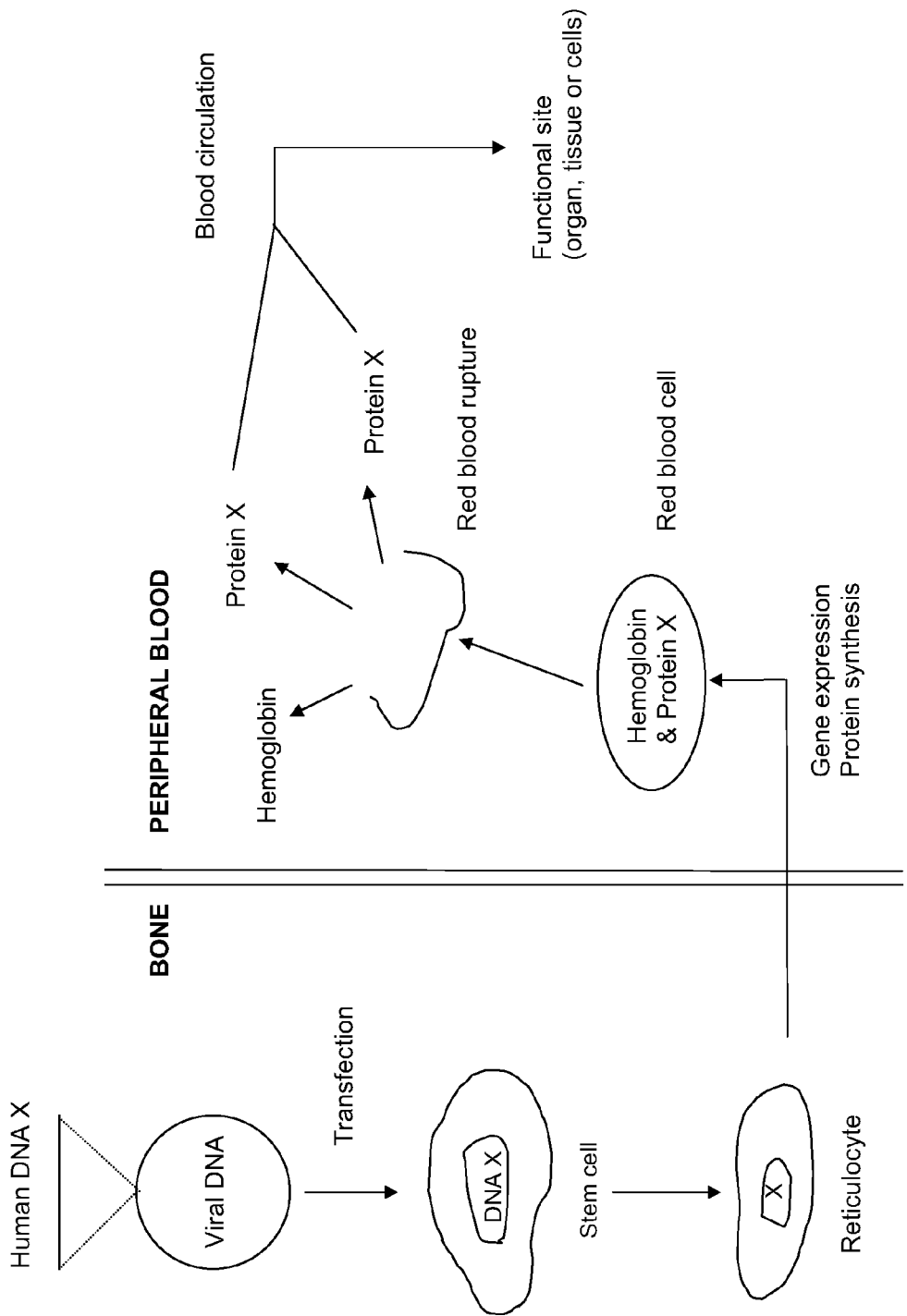
FIG. 1 is a schematic description of one embodiment of the present invention.

The present invention provides a method for producing and delivering protein in vivo. In one embodiment, the method comprises steps of: (1) insert a promoter and a gene encoding a protein in a vector; (2) collect an amount of mammalian host cells from a mammal; (3) treat the host cells in vitro with the vector described above; (4) introduce the treated host cells back to the mammal. After reintroduction of the treated host cells back into the mammal, the treated host cells produce red blood cells and the protein in vivo, wherein the protein is contained only in the red blood cells. The red blood cells rupture at the end of their life cycle and release the protein into blood stream. Optionally, one or more enhancers, in addition to the promoter, may also be inserted into the vector.

For the purpose of the present invention, the host cells are stem cells, and other progenitor cells of red blood cells. Bone marrow is a suitable source of stem cells, and is advantageous in that it contains the precursors of red blood cells. The vector DNA may be inserted into the mammalian host cells by any gene transfer method known in the art, for example retroviral-mediated gene transfer, electroporation, microinjection, cell fusion, or protoplast fusion.

The term "vector" as used herein connotes in its broadest sense any recombinant DNA material capable of transferring DNA from one cell to another. The vector can be a single piece of DNA in linear or circular form, and can, in addition to the essential functional elements of the invention, include such other sequences as are necessary for particular applications. For example, the vector may contain additional features such as a selectable marker gene or genes, and/or features which assist translation or other aspects of the production of a cloned product.

Preferably, the vector is a viral vector. The viral vector is depleted of segments responsible for viral expression, i.e., replication-incompetent. More preferably, the vector is a retroviral vector, a lentiviral vector, and an adenoviral vector.

The term "promoter" as used herein connotes in its broadest sense any promoter which enables initiation of a gene to express a protein in the progenitor cells of the red blood cells. The promoter could be a natural promoter of a gene, or a mutated promoter of a gene. A natural promoter is the promoter present in the gene of a protein that is native to the cell. Optionally, the promoter may be present in tandem with another promoter, and may include one or more enhancer elements. Preferably, the promoter is a hemoglobin promoter.

The term "enhancer" as used herein connotes in its broadest sense any enhancer capable of increasing the utilization of promoters, and functioning in either orientation and in any location (upstream or downstream) relative to the promoter.

The term "gene" as used herein is a DNA sequence, preferably a structural gene encoding a protein. The protein for the purpose of the present invention includes, but not limited to, antibody, enzyme, cofactor, interferon, hormone, and peptide. Furthermore, the protein includes natural protein, fusion protein and mutated protein. The protein can be entirely heterologous to the host cell. The protein may also be a commercially useful polypeptide or peptide, such as a pharmaceutical.

The term "heterologous" and "non-native" as used herein mean that a gene or a protein is not naturally present, or a biological process is not naturally occurred in the host cells.

In another embodiment, the method comprises steps of: (1) insert a hemoglobin promoter and a gene encoding a non-hemoglobin protein in a vector; (2) collect an amount of mammalian host cells from a mammal; (3) treat the host cells in vitro with the vector described above, (4) introduce the treated host cells back to the mammal. After reintroduction of the treated host cells back into the mammal, the host cells produce red blood cells in vivo. The protein is contained only in the red blood cells because the inserted hemoglobin promoter in the vector is active only in the precursors of the red blood cells. The red blood cells rupture at the end of their life cycle and release the protein into blood stream.

Naturally, red blood cells are generated in bone marrow by stem cells. Stem cells, a subset of cells in the marrow, give rise to the full spectrum of blood cells and replace dead cells throughout a person's life.

Red blood cells move into peripheral blood in a few days after being produced in the marrow. Mature red blood cells contain mainly hemoglobin, and cytoplasm. There is no nucleus in mature red blood cells. The primary function of red blood cells is to supply oxygen carried by hemoglobin into the body. The half life of red blood cells is about 60 days in peripheral blood. At the end of the red blood cell life cycle, red blood cells rupture in the spleen and release hemoglobin into the blood stream. Released hemoglobin is collected in the liver and reused in red blood cell production.

Hemoglobin is a very stable protein. It has been used as a carrier for drug delivery (U.S. Pat. No. 5,759,517). Hemoglobin is only produced in red blood cells and it is retained in the circulation of peripheral blood.

The method of the present invention is novel in the production of a protein and particularly in the delivery of a protein to the body. With the method of the present invention, a protein is produced only by the progenitor cells of the red blood cells and carried by the red blood cells, instead of in tissue specific cells conventionally used in gene therapy. Unlike prior art's tissue specific approach, the method of the present invention bypasses the process of delivering the gene encoding protein into specific organ or tissue for protein production. The method uses hemoglobin to control the protein production only in the progenitor cells of the red blood cells, and then uses the red blood cells as a vehicle to deliver the protein to its functional sites.

With the method of the present invention the protein is contained in red blood cells without being exposed to extra-cellular environment or to an enzymatic environment of nucleated blood cells. The protein is protected by the cell membrane from interaction with extra-cellular environment until rupture of the red blood cells. In the prior art when the naked DNA and liposome methods are used to deliver DNA, DNA degrades after induced into the body of a patient or an animal. The method of the present invention prevents the protein from being exposed to harsh environment, and provides stabilization of the proteins after completion of their synthesis in vivo.

In the aspect of protein delivery, the method of the present invention uses red blood cells for additional function of a transport vehicle for protein delivery. The method utilizes red blood cell's natural rupture to deliver produced proteins into the blood stream. The mechanism of protein delivery by the method of the present invention is fundamentally different from natural cell secretion or regulated exocytosis.

The method of the present invention has several advantages. First, the method of the present invention provides efficient protein synthesis and enables an amount of protein production sufficient for therapeutic purpose. More specifically, once a gene is introduced into a stem cell, such as through transfection or transduction, the stem cell will produce red blood cells, and synthesize the protein continuously. This means that even when a small portion of stem cells, among all stem cells treated, achieve a successful gene transfection or transduction, the numbers of red blood cells produced by these stem cells will contain sufficient amount of protein. Since the red blood cell production is a continuous process, the protein is also synthesized in a continual manner.

Using the method of the present invention, a protein is produced by the progenitor cells of the red blood cells, and carried by the red blood cells for delivery. Once the red blood cells that carry the protein release into the peripheral blood, the red blood cells themselves have no ability to further express protein. The red blood cells are the temporary storage sites for the protein until the protein is released out when the red blood cells rupture. This is a major distinction between red blood cells and other nucleated blood cells. The later is capable of protein expression in the peripheral blood.

Second, the red blood cells provide a natural protection to the protein against degradation. The protein is only contained in the red blood cells because the hemoglobin promoter is active only in the progenitor cells of the red blood cells. Red blood cells do not have a nucleus. Hence, the produced protein will not be degraded by nuclear enzymes. Compared to other nucleated cells, such as white blood cells, the protein will be more stable in the red blood cells. Example of the protein stability in the red blood cells is demonstrated by natural hemoglobin through the life cycle of red blood cells. In addition, the red blood cells also protect the proteins from extra-cellular environment before the proteins enter into the blood circulation.

Third, the method of the present invention provides an efficient protein delivery mechanism. Natural red blood cells have a half life about 60 days in peripheral blood. Therefore, by utilizing red blood cell rupture as the delivery mechanism the protein supply will be continuous and constant. For certain diseases, for instance, hemaphilia and hormone related diseases, continuous protein supply is desired. For other diseases, such as cancer, a constant protein supply not only provide a treatment, but may also contribute to the prevention of the disease. Furthermore, in some cases although a constant protein supply may not be the mode of natural supply, it could be therapeutic and beneficial. A suitable example of such case is insulin supply of diabetes patients.

Fourth, the method of the present invention delivers the proteins without the limitations of natural cell function. More specifically, the method avoids the difficulty in protein export or delivery by the host cells, if the host cells used are not the cells of the specific organ or tissue that naturally produce the protein. For example, certain proteins generated in skin tissue by genetic method have to be adequately released from the host skin tissue cells before it can be used in the blood stream for therapeutic purpose. Since the host cells are not the original organ or tissue cells in the natural protein production process, they may not have secretion function to export a specific guest protein. In the later case, the guest protein will accumulate in the host cells and cause cell death eventually.

The method of the present invention utilizes the natural rupture of red blood cells for delivery of a protein. Alternatively, the rupture of the red blood cells can also be induced if desired. For instance, the life cycle time of the red blood cells can be modified by genetic mutation. The method of the present invention supplies the protein through red blood cell circulation in peripheral blood. For therapeutic purpose, it will retain the protein in the blood stream better than other conventional protein carriers.

Fifth, with the method of the present invention, the amount of protein production and delivery can be controlled by the amount of host cells collected and treated. When the stem cells are collected from bone marrow, the treated bone marrow can be implanted at the original collection position, or enclosed in a sag, then implanted back into a patient's bone marrow. If a large quantity of protein is needed, such as human serum albumin, the amount of protein production can be controlled by the numbers of transplant sites. If a patient inherits a genetic defect and needs a continuing supply of the normal gene product throughout life, a permanent implantation could be selected. If only short term activity of a gene is needed, such as to activate the immune system against cancer cells or an infectious agent, the sag can be taken out from the body when the therapy is complete, or no longer desired.

Sixth, with the method of the present invention, the protein is only present in the red blood cells. Once treated stem cells are taken out from the body, their red blood cell production will stop instantly. The remaining red blood cells in the peripheral blood, which carry the protein, will rupture at the end of their life cycle. By then, the supply of the protein will stop completely. Therefore, the method of the present invention provides a simple safety control mechanism for the therapeutic process.

As discussed above, the mature red blood cells themselves do not express protein. There is no protein production after the red blood cells release into peripheral blood from the bone marrow. Different from the red blood cells, nucleated blood cells, such as leukocytes, express proteins in the peripheral blood until the cells die or lost the function. Therefore, when genetically engineered nucleated blood cells are introduced into blood circulation, there is no control of the protein production. More particularly, when the protein is heterologous to the host nucleated cells, the compatibility or interactions between the foreign protein and native proteins, and nuclear enzymes throughout the cell life could be a safety concern of the gene therapy. On the other hand, since the red blood cells do not produce protein in the peripheral blood, the protein production is confined in the parent stem cells, which can be controlled by the amount of transplant.

The method of the present invention has a broad spectrum of applications, particularly suitable for gene argumentation therapy, in which a healthy gene replaces the product of a missing or defective gene but does not physically replace the flawed DNA itself. An example of gene therapy using the method of the present invention is to treat a haemophilia patient. In this case, a retroviral vector will be constructed with a hemoglobin promoter and haemophilia factor XIII gene. Then, an amount of bone marrow is collected from the patient and the stem cells is transduced with the vector. The vector construction and gene transduction can be accomplished using procedures known in the art. The bone marrow after treatment then is transplanted back into the patient. After transplantation, the transduced stem cells will produce blood cells. The haemophilia factor XIII will be produced only in the red blood cells which will circulate in the peripheral blood of the patient under treatment. At the end of life cycle of these red blood cells, haemophilia factor XIII will be released into bloodstream upon the rupture of the red blood cells. Because of a continuous generation of red blood cells by the transduced stem cells and continual red blood cell rupture at the end of their life cycle, the patient under such therapy will have continuous supply of haemophilia factor XIII.

The success of the gene expression and protein delivery process described above can be measured stepwise by whole blood cell haemophilia factor XIII DNA PCR assay, red blood cell protein immuno-assay or color staining assay, and serum protein immuno-assay or color staining assay. A positive whole blood cell haemophilia factor XIII DNA PCR assay result indicates the success of gene expression in vivo. A positive red blood cell protein immuno-assay or staining assay result indicates the success of protein production in the red blood cells produced by the transduced stem cells. A positive serum protein immuno-assay or staining assay indicates the success of the protein delivery into blood stream after the gene expression and protein production in vivo.

The method of the present invention has broad scope of applications in treating diseases, either inherited genetically or acquired diseases. In general, any protein that either has a function in blood stream, such as hemophilia factor XIII, or can be delivered to functional site through blood stream, such as hormones, can be supplied by using the method of the present invention. Several types of applications can be classified, where the method of the present invention can be utilized to supply desired proteins, which may or may not link to a disease.

One suitable type of application is to treat inherited diseases. Such diseases include, but are not limited to, cystic fibrosis, duchenne muscular dystrophy, hemophilia A, Huntington's disease, familial hypercholesterolemia, and fragile-X syndrome. The second type of application is to provide a protein that functions as an enzyme for the treatment of other diseases, such as Gauchers disease. The third type of application is to provide the protein that functions as a hormone. Suitable examples of this type of proteins are thyroid hormone, growth hormone, and diabetes. The fourth type of application is to treat decreased protein level caused by certain conditions. Suitable examples in this application are low level of human serum albumin produced by liver, low level of hemoglobin stimulation factor, cortisol deficiency, and aldosterone deficiency caused by certain kidney conditions. Certain pituitary gland conditions caused growth hormone deficiency, gonadotropin deficiency, thyroid stimulating hormone deficiency, and adrenal cortex deficiency are also examples that can be treated by the instant method. The fifth type of application is to provide a mammalian or a non-mammalian protein that has a therapeutic function. Suitable examples of such proteins include animal protein (e.g. snake), micro-organism protein (e.g. interferon), and plant protein with a therapeutic function.

The sixth type of application is to provide proteins related to cancers. Suitable examples of proteins are anti-oncogene (tumor inhibitor) protein, tumor necrosis gene protein, and interferon. It is known that in different types of cancer patients, certain proteins are missing or low in concentration in comparison to normal subjects. Lack of certain proteins may be responsible for malignant cell growth, or may cause severe damage of the immune or metabolic system of the cancer patient. With the method of the present invention, a supply of certain protein can have therapeutic effects in the former case, or reduce symptoms or complications for the latter. Moreover, a supply of certain proteins can also provide a prevention of certain types of cancers. More specifically, this function is particularly suitable for those cancer high risk populations that inherit genetic defects in their natural protein production capability. Well known examples are breast cancer, ovarian cancer, and prostate cancer. The tissue specific method described previously may not be able to function in such situation, because the target tissue or cells may not be compatible with gene-transferred cells due to the genetic defects. Therefore, the method of the present invention could provide a significant clinical value in this type of application.

The seventh type application is to provide proteins to treat immune system diseases. Suitable examples of diseases are antibody deficiency syndromes, such as Bruton's agammaglobinemia (reduced IgG, IgM, and IgA), common variable immunodeficiency (reduced IgG, IgM, and IgA), and selective IgA deficiency (reduced IgA). Another example is the phagocyte disorders, such as C1r, C1q, C2 defection, C4 defection, C3 defection, and C5-C9 defection. The eighth type of application is to provide mutated, fused and synthetic proteins.

The method of using the progenitor cells of red blood cells as the host cells for protein production and descendent red blood cells for protein delivery can be applied similarly to other cell types. For example, one can use a specific promoter to control the production of a protein in megakaryocytes (the precursor of platelet) by the stem cells in the same manner described in the above embodiment. The protein will be delivered into the blood stream when megakaryocytes rupture in vivo.

The method of the present invention is further described by following example, which is intended to be illustrative and not limiting.

EXAMPLE

(a) Construction of a Retroviral Vector with Beta-Gal Gene

Figure 2:
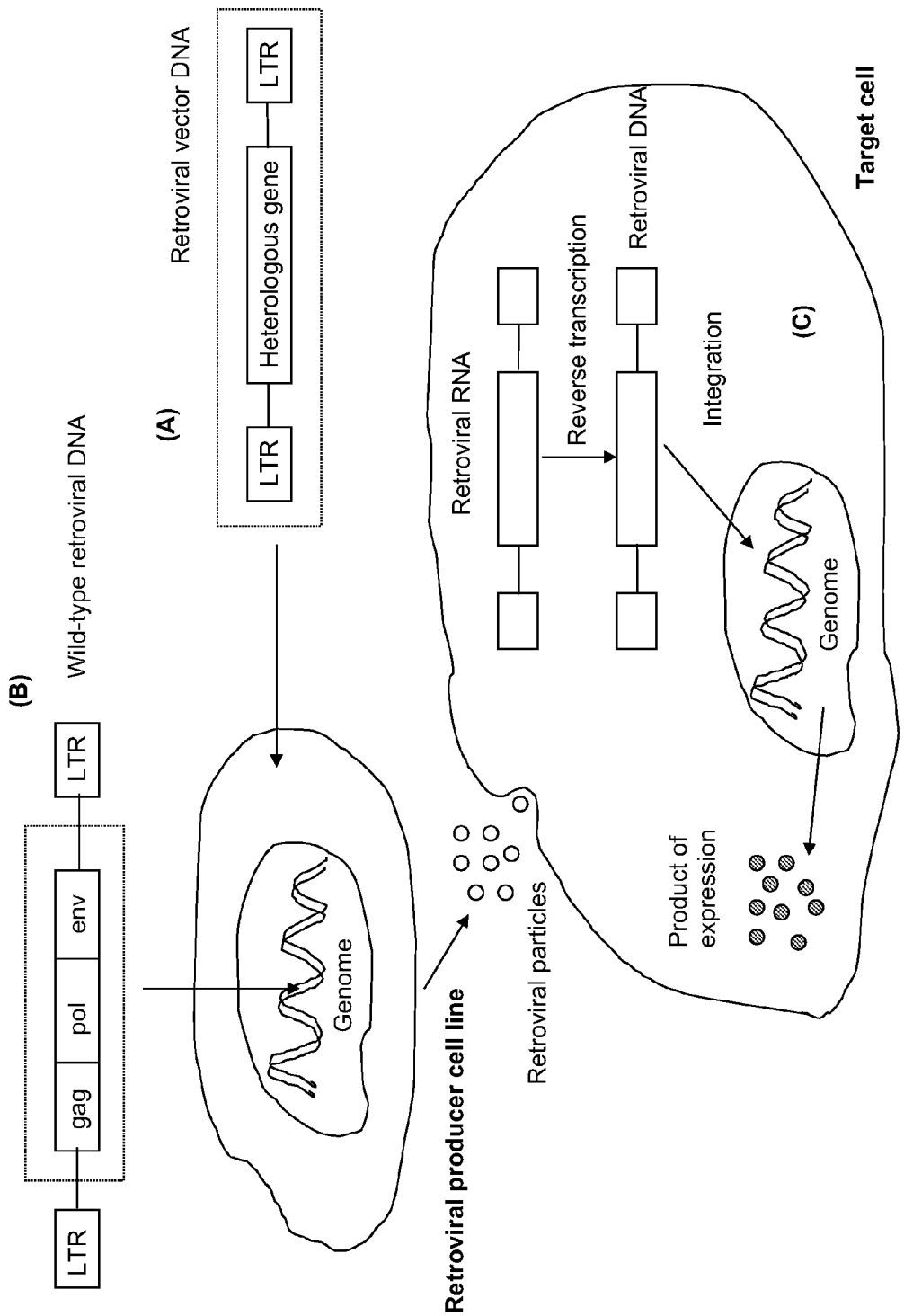
FIG. 2 is the illustrations of the construction of a retroviral vector with beta-gal gene described in the example.

First, a retroviral vector containing the psi sequence (the packaging function of a retrovirus) and a heterologous gene (in this case beta-gal) will be constructed using the recombinant method known in the art. In the retroviral vector, the gag, pol and env genes of the retrovirus will be replaced by the heterologous gene (FIG. 2, (A)). A viral producer cell line will also be created, which contains certain wild type retroviral genes, such as gag, pol and env, in trans configuration (FIG. 2, (B)). Thereafter, the above retroviral vector will be used to transduce the producer cell line. The transduction results in the production of a replication-incompetent retroviral particle carrying a vector that contains a heterologous gene (in this case a beta-gal gene). The retroviral particle is able to bind to a target cell (in this case the stem cell) and to insert its components into the cell. In the cell, retroviral RNA will be changed to DNA by reverse transcription. The retroviral DNA will be inserted into cell genome by integration (FIG. 2, (C)).

Two retroviral vectors will be constructed as described above. Both retroviral vectors contain the same beta-gal gene. The only difference between these two retroviral vectors will be the promoter or/and the enhancer. The first retroviral vector contains a SV40 promoter upstream of the beta-gal gene. The vector is able to express beta-gal gene in almost all mammalian (human and animal) cells. The second retroviral vector has a hemoglobin promoter upstream of the beta-gal gene. This retroviral vector is able to express beta-gal gene only in the red blood cells.

In addition, two control retroviral vectors will also be constructed. The control retroviral vector will have either a SV40 promoter or a hemoglobin promoter. However, both control retroviral vectors will not contain the beta-gal gene.

The producer cell line transduced by the beta-gal gene containing retroviral vector will then be cultured in the standard cell culture medium at 37° C. Retroviral_particles will release from the producer cell line into the cultured medium. The retroviral particles will be collected from the culture medium by centrifugation. The collected particles will be analyzed by DNA analysis to confirm the production of the beta-gal retroviral particles.

The transduction efficiency of the beta-gal retrovirus and beta-gal protein expression by above described process on human cells will be first tested on commercial available human cell lines. Based on the characteristics of the beta-gal protein, the transduction results can be confirmed by color staining assay known in the art.

(b) Transduction of Bone Marrow Cells with Beta-Gal Retrovirus

Rabbits or dogs will be used as the testing and control subjects. Bone marrow will be collected from hipbone of the subject by surgery under anesthesia.

The stem cells will be isolated from the bone marrow using the known method in the art, such as density gradient method. The stem cells will be cultured in the culture dishes or bottles under standard cell culture conditions. After two to three days of culturing, the testing viruses (SV40 promoter with beta-gal gene, and hemoglobin promoter with beta-gal gene), and control viruses (SV 40 promoter without beta-gal gene, and hemoglobin promoter without beta-gal gene) produced as described above will be added into the cell culture for transduction. After five to seven day's transduction, a sample of the transduced cells will be analyzed using beta-gal DNA analysis to determine the efficiency of transduction. The remaining transduced cells will also be analyzed using beta-gal protein analysis to determine the efficiency of beta-gal gene expression.

The transduced stem cells will then be transplanted back into the subject. The locations of these transplants will be marked as identification marks for future removal of the transplanted cells.

(c) Results of Gene Expression and Protein Delivery In Vivo

After bone marrow transplant, peripheral whole blood samples will be collected, at appropriate interval, from the testing and control subjects. The red blood cells and white blood cells will be separated from the whole blood samples of the testing and control subjects by conventional method. The separated cells will be washed to deplete residue serum and then will be lysed by a lysing reagent. The supernatant will be analyzed by the beta-gal protein assays or color staining assay.

For the subject that has a transplantation of the cells transduced with the first testing vector, a positive beta-gal protein assay will be obtained in the supernatants of both red blood cells and white blood cells. On the other hand, for the testing subject that has a transplantation of the cells transduced with the second testing vector a positive beta-gal protein assay will only be obtained in the supernatants of red blood cells. For the subjects that have a transplantation of the cells transduced with the control vectors, the beta-gal protein assay result will be negative.

In addition, for the testing subject that has a transplantation of the cells transduced with the second testing vector, serum will be separated by centrifugation of the whole blood samples and will be analyzed by immunoassay or color staining assay. A positive serum beta-gal protein assay result indicates the success of (1) gene expression in stem cells and red blood cell production by the transduced stem cells, (2) protein production in the red blood cells, and (3) the protein delivery into the blood stream, i.e., released from the red blood cells.

The invention has been described with reference to the preferred embodiments. It should be understood, however, that the invention is not so limited, and the scope of the invention should be determined with reference to the following claims, rather than to the foregoing specification.

All patents and publications referred to in this application are hereby incorporated by reference in their entirety.

What is claimed is:

1. A method for producing protein and delivering the protein in the bloodstream of a mammal comprising the steps of:
    (a) inserting into a viral vector a globin promoter and a gene encoding a protein which is non-native to red blood cells, wherein said promoter and said gene are operably linked; and wherein said protein is a member selected from the group consisting of an antibody, enzyme, cofactor, interferon, peptide, and hormone;
    (b) collecting an amount of progenitor cells of red blood cells from said mammal;
    (c) transfecting said progenitor cells of red blood cells in vitro with said vector containing said promoter and said gene; and
    (d) introducing the transfected progenitor cells of red blood cells back into said mammal, wherein the transfected progenitor cells of red blood cells produce altered red blood cells containing said protein which is non-native to red blood cells in vivo in said mammal, and wherein said protein which is non-native to red blood cells is contained only in said altered red blood cells, and thereafter said protein which is non-native to red blood cells is released into said bloodstream of said mammal through induced rupture of said altered red blood cells in said bloodstream.

2. The method of claim 1 further comprising inserting an enhancer in said viral vector.

3. The method of claim 1 wherein said viral vector is selected from the group consisting of a retroviral vector, an adenoviral vector and a lentiviral vector.

4. The method of claim 1, wherein said progenitor cells of red blood cells are stem cells collected from the bone marrow of said mammal.

* * * * *